United States Patent
Norris (12) 
(10) Patent No.: US 8,988,911 B2
(45) Date of Patent: Mar. 24, 2015

(54) SELF-BIAS EMITTER CIRCUIT

(71) Applicant: Parametric Sound Corporation, Poway, CA (US)

(72) Inventor: Elwood G. Norris, Poway, CA (US)

(73) Assignee: Turtle Beach Corporation, Poway, CA (US)

( * ) Notice: Subject to any disclaimer, the term of this patent is extended or adjusted under 35 U.S.C. 154(b) by 0 days.

(21) Appl. No.: 13/917,315

(22) Filed: Jun. 13, 2013

(65) Prior Publication Data

US 2014/0369531 A1 Dec. 18, 2014

(51) Int. Cl.
*H02M 7/06* (2006.01)
*H04R 3/00* (2006.01)

(52) U.S. Cl.
CPC .......................................... *H04R 3/00* (2013.01)
USPC .......................................................... 363/126

(58) Field of Classification Search
CPC ............................... H02M 7/064; H02M 7/066
USPC ........... 363/125, 126; 323/358, 359; 330/290, 330/297, 298
See application file for complete search history.

(56) References Cited

U.S. PATENT DOCUMENTS

| | | |
|---|---|---|
| 1,616,639 A | 2/1927 | Sprague |
| 1,764,008 A | 6/1930 | Crozier |
| 1,799,053 A | 3/1931 | Mache |
| 1,809,754 A | 6/1931 | Steedle |
| 1,951,669 A | 3/1934 | Ramsey |
| 1,983,377 A | 12/1934 | Kellogg |
| 2,461,344 A | 2/1949 | Olson |
| 2,855,467 A | 10/1958 | Curry |
| 2,872,532 A | 2/1959 | Buchmann et al. |
| 2,935,575 A | 5/1960 | Bobb |
| 2,975,243 A | 3/1961 | Katella |

(Continued)

FOREIGN PATENT DOCUMENTS

| | | |
|---|---|---|
| JP | H2265400 | 10/1990 |
| JP | 2005/353989 A | 12/2005 |

(Continued)

OTHER PUBLICATIONS

Aoki et al; Parametric Loudspeaker-Characteristics of Acoustic Field and Suitable Modulation of Carrier Ultrasound; Electronics and Communications in Japan; 1991, Part 3, vol. 74, No. 9, pp. 76-82.

(Continued)

*Primary Examiner* — Matthew Nguyen (57) ABSTRACT

Self-bias emitter circuit configurations can use the amplitude of an input AC carrier signal to provide a DC bias voltage across an emitter for suitable operation. A self-bias emitter circuit can include a transductor with primary matched with an amplifier, while secondary can be matched to the emitter. Self-bias emitter circuit can also include a full-wave bridge rectifier or a center tap inductor in conjunction with two diodes to rectify the AC carrier signal into a corresponding DC voltage. This DC voltage can be subsequently filtered by a capacitor to provide a steady DC bias voltage across the emitter. Sufficiently small, decoupling capacitors can be installed at each side of the full-wave rectifier in order to decouple the DC bias voltage, while a sufficiently large capacitor can be installed between the emitter and secondary for preventing the applied DC bias voltage from flowing back to secondary.

18 Claims, 7 Drawing Sheets

(56) References Cited

U.S. PATENT DOCUMENTS

| | | |
|---|---|---|
| 2,975,307 A | 3/1961 | Schroeder et al. |
| 3,008,013 A | 11/1961 | Williamson et al. |
| 3,012,222 A | 12/1961 | Hagemann |
| 3,136,867 A | 6/1964 | Brettell |
| 3,345,469 A | 10/1967 | Rod |
| 3,373,251 A | 3/1968 | Seeler |
| 3,389,226 A | 6/1968 | Peabody |
| 3,398,810 A | 8/1968 | Clark, III |
| 3,461,421 A | 8/1969 | Stover |
| 3,544,733 A | 12/1970 | Reylek |
| 3,612,211 A | 10/1971 | Clark, III |
| 3,613,069 A | 10/1971 | Cary, Jr. |
| 3,654,403 A | 4/1972 | Bobb |
| 3,674,946 A | 7/1972 | Winey |
| 3,710,332 A | 1/1973 | Tischner et al. |
| 3,723,957 A | 3/1973 | Damon |
| 3,742,433 A | 6/1973 | Kay et al. |
| 3,787,642 A | 1/1974 | Young, Jr. |
| 3,816,774 A | 6/1974 | Ohnuki et al. |
| 3,821,490 A | 6/1974 | Bobb |
| 3,829,623 A | 8/1974 | Willis et al. |
| 3,833,771 A | 9/1974 | Collinson |
| 3,836,951 A | 9/1974 | Geren et al. |
| 3,892,927 A | 7/1975 | Lindenberg |
| 3,919,499 A | 11/1975 | Winey |
| 3,941,946 A | 3/1976 | Kawakami et al. |
| 3,997,739 A | 12/1976 | Kishikawa et al. |
| 4,056,742 A | 11/1977 | Tibbetts |
| 4,064,375 A | 12/1977 | Russell et al. |
| 4,146,847 A * | 3/1979 | Otao et al. .................. 330/297 |
| 4,160,882 A | 7/1979 | Driver |
| 4,207,571 A | 6/1980 | Passey |
| 4,210,786 A | 7/1980 | Winey |
| 4,242,541 A | 12/1980 | Ando |
| 4,245,136 A | 1/1981 | Krauel, Jr. |
| 4,284,921 A | 8/1981 | Lemonon et al. |
| 4,289,936 A | 9/1981 | Civitello |
| 4,295,214 A | 10/1981 | Thompson |
| 4,314,306 A | 2/1982 | Darrow |
| 4,322,877 A | 4/1982 | Taylor |
| 4,369,490 A * | 1/1983 | Blum .......................... 363/48 |
| 4,378,596 A | 3/1983 | Clark |
| 4,385,210 A | 5/1983 | Marquiss |
| 4,418,404 A | 11/1983 | Gordon et al. |
| 4,419,545 A | 12/1983 | Kuindersma |
| 4,429,193 A | 1/1984 | Busch-Vishniac et al. |
| 4,439,642 A | 3/1984 | Reynard |
| 4,471,172 A | 9/1984 | Winey |
| 4,480,155 A | 10/1984 | Winey |
| 4,514,773 A | 4/1985 | Susz |
| 4,550,228 A | 10/1985 | Walker et al. |
| 4,558,184 A | 12/1985 | Busch-Vishniac et al. |
| 4,593,160 A | 6/1986 | Nakamura |
| 4,593,567 A | 6/1986 | Isselstein et al. |
| 4,672,591 A | 6/1987 | Breimesser et al. |
| 4,673,888 A | 6/1987 | Engelmann et al. |
| 4,695,986 A | 9/1987 | Hossack |
| 4,716,353 A * | 12/1987 | Engelmann .................. 320/139 |
| 4,751,419 A | 6/1988 | Takahata |
| 4,803,733 A | 2/1989 | Carver et al. |
| 4,823,908 A | 4/1989 | Tanaka et al. |
| 4,837,838 A | 6/1989 | Thigpen et al. |
| 4,872,148 A | 10/1989 | Kirby et al. |
| 4,885,781 A | 12/1989 | Seidel |
| 4,887,246 A | 12/1989 | Hossack et al. |
| 4,888,086 A | 12/1989 | Hossack et al. |
| 4,903,703 A | 2/1990 | Igarashi et al. |
| 4,908,805 A | 3/1990 | Sprenkels et al. |
| 4,939,784 A | 7/1990 | Bruney |
| 4,991,148 A | 2/1991 | Gilchrist |
| 5,018,203 A | 5/1991 | Sawyers et al. |
| 5,054,081 A | 10/1991 | West |
| 5,115,672 A | 5/1992 | McShane et al. |
| 5,142,511 A | 8/1992 | Kanai et al. |
| 5,153,859 A | 10/1992 | Chatigny et al. |
| 5,164,991 A * | 11/1992 | Johnson et al. .............. 381/120 |
| 5,210,803 A | 5/1993 | Martin et al. |
| 5,287,331 A | 2/1994 | Shindel et al. |
| 5,317,543 A | 5/1994 | Grosch |
| 5,357,578 A | 10/1994 | Taniishi |
| 5,361,381 A | 11/1994 | Short |
| 5,392,358 A | 2/1995 | Driver |
| 5,430,805 A | 7/1995 | Stevenson et al. |
| 5,487,114 A | 1/1996 | Dinh |
| 5,539,705 A | 7/1996 | Akerman et al. |
| 5,638,456 A | 6/1997 | Conley et al. |
| 5,684,884 A | 11/1997 | Nakaya et al. |
| 5,700,359 A | 12/1997 | Bauer |
| 5,859,915 A | 1/1999 | Norris |
| 5,885,129 A | 3/1999 | Norris |
| 5,889,870 A | 3/1999 | Norris |
| 6,011,855 A | 1/2000 | Selfridge et al. |
| 6,023,153 A * | 2/2000 | Fink .......................... 323/210 |
| 6,041,129 A | 3/2000 | Adelman |
| 6,106,399 A | 8/2000 | Baker et al. |
| 6,108,427 A | 8/2000 | Norris et al. |
| 6,151,398 A | 11/2000 | Norris |
| 6,188,772 B1 | 2/2001 | Norris et al. |
| 6,229,899 B1 | 5/2001 | Norris et al. |
| 6,241,612 B1 | 6/2001 | Heredia |
| 6,304,662 B1 | 10/2001 | Norris et al. |
| 6,411,015 B1 | 6/2002 | Toda |
| 6,498,531 B1 | 12/2002 | Ulrick et al. |
| 6,556,687 B1 | 4/2003 | Manabe |
| 6,584,205 B1 | 6/2003 | Croft, III et al. |
| 6,606,389 B1 | 8/2003 | Selfridge et al. |
| 6,628,791 B1 | 9/2003 | Bank et al. |
| 6,631,196 B1 | 10/2003 | Higgins |
| 6,775,388 B1 | 8/2004 | Pompei |
| 6,914,991 B1 | 7/2005 | Pompei |
| 6,940,468 B2 | 9/2005 | Aisenbrey |
| 6,975,731 B1 | 12/2005 | Cohen et al. |
| 7,158,646 B2 | 1/2007 | Bank et al. |
| 7,162,042 B2 | 1/2007 | Spencer et al. |
| 7,224,808 B2 | 5/2007 | Spencer et al. |
| 7,369,665 B1 | 5/2008 | Cheng |
| 7,536,008 B2 | 5/2009 | Howes et al. |
| 7,564,981 B2 | 7/2009 | Croft, III |
| 7,596,229 B2 | 9/2009 | Croft, III |
| 7,657,044 B2 | 2/2010 | Pompei |
| 7,667,444 B2 | 2/2010 | Mavay et al. |
| 7,729,498 B2 | 6/2010 | Spencer et al. |
| 7,850,526 B2 | 12/2010 | Mao |
| 7,957,163 B2 | 6/2011 | Hua |
| 8,027,488 B2 | 9/2011 | Pompei |
| 8,106,712 B2 | 1/2012 | Lee |
| 8,165,328 B2 | 4/2012 | Thomsen |
| 8,391,514 B2 | 3/2013 | Norris |
| 2001/0007591 A1 | 7/2001 | Pompei |
| 2004/0052387 A1 | 3/2004 | Norris et al. |
| 2005/0008168 A1 | 1/2005 | Pompei |
| 2005/0008268 A1 | 1/2005 | Plourde et al. |
| 2005/0086058 A1 | 4/2005 | Lemelson et al. |
| 2005/0100181 A1 | 5/2005 | Croft, III et al. |
| 2005/0152561 A1 | 7/2005 | Spencer |
| 2005/0195985 A1 | 9/2005 | Croft, III et al. |
| 2005/0220311 A1 | 10/2005 | Sun et al. |
| 2006/0025214 A1 | 2/2006 | Smith |
| 2006/0215841 A1 | 9/2006 | Vieilledent et al. |
| 2007/0154035 A1 | 7/2007 | Fukui |
| 2007/0211574 A1 | 9/2007 | Croft, III |
| 2008/0261693 A1 | 10/2008 | Zalewski |
| 2008/0279410 A1 | 11/2008 | Cheung et al. |
| 2010/0016727 A1 | 1/2010 | Rosenberg |
| 2010/0040249 A1 | 2/2010 | Lenhardt |
| 2010/0041447 A1 | 2/2010 | Graylin |
| 2010/0166222 A1 | 7/2010 | Bongiovi |
| 2010/0302015 A1 | 12/2010 | Kipman et al. |
| 2010/0303263 A1 | 12/2010 | Hiensch |
| 2011/0018710 A1 | 1/2011 | Booij et al. |
| 2011/0044467 A1 | 2/2011 | Pompei |
| 2011/0051977 A1 | 3/2011 | Losko et al. |
| 2011/0077080 A1 | 3/2011 | Meer |
| 2011/0103614 A1 | 5/2011 | Cheung et al. |

(56) References Cited

U.S. PATENT DOCUMENTS

| | | |
|---|---|---|
| 2011/0109248 A1 | 5/2011 | Liu |
| 2011/0212777 A1 | 9/2011 | Chen |
| 2011/0216928 A1 | 9/2011 | Eisenberg et al. |
| 2012/0029912 A1 | 2/2012 | Almagro |
| 2012/0051556 A1 | 3/2012 | Pompei |
| 2012/0057734 A1 | 3/2012 | Schulein |
| 2012/0148070 A1 | 6/2012 | Norris |
| 2012/0148082 A1 | 6/2012 | Norris |
| 2014/0104988 A1 | 4/2014 | Norris |
| 2014/0133668 A1 | 5/2014 | Podoloff |
| 2014/0161282 A1 | 6/2014 | Norris |
| 2014/0161291 A1 | 6/2014 | Matsuzawa |

FOREIGN PATENT DOCUMENTS

| | | |
|---|---|---|
| WO | WO01/08449 | 2/2001 |
| WO | WO01/15491 | 3/2001 |
| WO | WO01/52437 | 7/2001 |
| WO | WO 2008/046175 A1 | 4/2008 |
| WO | WO 2013/158298 | 10/2013 |

OTHER PUBLICATIONS

Berktay et al; Possible Exploitation of Non-Linear Acoustics in Underwater Transmitting Applications; Apr. 13, 1965; vol. 2, No. 4, pp. 435-461.
Crandall et al; The Air-Damped Vibrating System: Theoretical Calibration of the Condenser Transmitter; American Physical Society; Dec. 28, 1917; pp. 449-460.
Makarov et al; Parametric Acoustic Nondirectional Radiator; Acustica; 1992; vol. 77, pp. 240-242.
PCT Application PCT/US2013/021064; Filed Jan. 10, 2013; Parametric Sound Corporation; International Search Report Mailed May 16, 2013.
U.S. Appl. No. 13/738,887, filed Jan. 10, 2013; Elwood G. Norris.
U.S. Appl. No. 13/917,273, filed Jun. 13, 2013; Elwood G. Norris.
U.S. Appl. No. 13/935,246, filed Jul. 3, 2013; Elwood G. Norris.
U.S. Appl. No. 13/160,051, filed Jun. 14, 2011; Elwood G. Norris; Office Action issued Jul. 19, 2013.
Wagner; Electrostatic Loudspeaker Design and Construction; Audio Amateur Press Publishers; 1993; Chapters 4-5; pp. 59-91.
Westervelt; Parametric Acoustic Array; The Journal of the Acoustical Society of America; Apr. 1963; vol. 35, No. 1, pp. 535-537.
Yoneyama et al.; The Audio Spotlight: An Application of Nonlinear Interaction of Sound Waves to a New Type of Loudspeaker Design; Acoustical Society of America; 1983; vol. 73, No. 5; pp. 1532-1536.
U.S. Appl. No. 13/160,048, filed Jun. 14, 2011; Elwood G. Norris; office action dated Oct. 1, 2013.
U.S. Appl. No. 13/160,051, filed Jun. 14, 2011; Elwood G. Norris; office action dated Oct. 31, 2013.
U.S. Appl. No. 13/761,484, filed Feb. 7, 2013; Elwood G. Norris; office action dated Nov. 4, 2013.
U.S. Appl. No. 13/761,484, filed Feb. 7, 2013; Elwood G. Norris.
U.S. Appl. No. 13/801,718, filed Mar. 13, 2013; Elwood G. Norris.
U.S. Appl. No. 13/863,971, filed Apr. 16, 2013; Elwood G. Norris.
EP Application EP 11796319.9; filing date Jun. 14, 2011; Elwood G. Norris; European Search Report dated Jul. 29, 2014.
PCT Application PCT.US2014/037786; filing date May 13, 2014; Parametric Sound Corporation; International Search Report mailed Sep. 11, 2014.
PCT Application PCT/US2014/018691; filing date Mar. 26, 2014; Parametric Sound Corporation; International Search report mailed Jun. 6, 2014.

\* cited by examiner

SELF-BIAS EMITTER CIRCUIT

BACKGROUND

1. Field of the Invention

The present disclosure relates generally to parametric loudspeakers for use in audio production, and more particularly, to emitter circuit configurations.

2. Background Information

A new form of emitters can include a film made of plastic materials such as kapton, mylar, and polypropylene, among others. The upper side of this film can be laminated with a conductive material such as copper, nickel, aluminum, or gold.

The emitter can also include a back plate or stator which can be configured to exhibit a plurality of microscopic slots or pits arranged in a random pattern. The lower side of the stator can be metallized to receive the application of voltage.

Both film and stator can be combined in such a way that the non-metalized side of the film or lower side can be in contact with the upper side of the stator that exhibits the plurality of microscopic slots or pits. A DC bias voltage can be applied to the metalized side or upper side of the film and the metalized or lower side of the stator, where both conductive sides of film and stator can be separated by the film since its lower side is not metallized. When the DC bias voltage is applied to the emitter, the metalized side of the stator can pull the film down to the cavities of the microscopic slots or pits, causing the emitter to activate. As such, DC bias voltage application can be required for a suitable emitter operation.

To provide DC bias voltage, an auxiliary power supply can be operatively connected to the emitter, but this configuration can increase the cost of the emitter circuit while also implying the use of additional wires to connect the emitter with the auxiliary power supply.

For the foregoing reasons, there is a need for providing a suitable application of DC bias voltage to a new emitter configuration.

SUMMARY

A self-bias emitter circuit can receive a modulated or unmodulated AC carrier signal as input and can subsequently rectify this modulated or unmodulated AC carrier signal into a steady DC bias voltage for suitable application across an emitter device without affecting carrier information necessary to the emitter to emit parametric information.

According to an embodiment, a self-bias emitter circuit can include a transductor with an electromagnetic shielded pot core, where its primary can be matched to the impedance of an amplifier, while its secondary is matched to the impedance of the emitter to provide a chosen resonant point. This self-bias emitter circuit can include a full-wave bridge rectifier that can convert the modulated or unmodulated AC carrier signal into a corresponding DC voltage. Subsequently, a filter capacitor can reduce variations of the DC voltage at the output of full-wave bridge rectifier in order to provide a steady DC bias voltage across the emitter for suitable operation. Sufficiently small, decoupling capacitors can be installed at each side of the full-wave rectifier to decouple the DC bias voltage from the secondary and to avoid shunting the AC carrier signal into the full-wave bridge rectifier. A sufficiently large capacitor can be installed between emitter and secondary to prevent DC bias voltage from flowing back to secondary.

Amplitude of DC bias voltage can approximately correspond to the highest peak of the AC carrier signal, where maximum achievable DC bias voltage can be determined by the highest peak of a modulated carrier signal.

According to another embodiment, a self-bias emitter circuit can include transductor with one primary and two secondary windings, where primary can be matched to the amplifier, while one secondary can be matched to the emitter. The other secondary can be operatively connected to the full-wave bridge rectifier which can convert an AC carrier signal into corresponding DC voltage, followed by smoothing of this DC voltage by filter capacitor for the application of suitable DC bias voltage across the emitter. Numbers of turns in the secondary connected with full-wave bridge rectifier can be selected according to the desired amplitude of the DC bias voltage.

In another embodiment, a self-bias emitter circuit can include transductor with primary matched to the amplifier, while the secondary can include an intermediate tap to configure one section of the secondary with a higher number of turns. Section of secondary with higher number of turns can be operatively connected to the full-wave rectifier to provide step-up voltage conversion, and consequently a higher DC bias voltage across the emitter. The other section of secondary can be configured for matching the emitter resonance.

Yet in another embodiment, a self-bias emitter circuit does not require the full-wave bridge rectifier for converting AC carrier signal into DC bias voltage. In such case, a center tapped inductor can be used as secondary in conjunction with two diodes for providing full-wave rectification of AC carrier signal, followed by filtering and application of DC bias voltage across the emitter.

In an even further embodiment, a self-bias emitter circuit does not require the full-wave bridge rectifier for converting AC carrier signal into DC bias voltage. In this particular embodiment, the self-bias emitter circuit can include a voltage doubler which can be used in conjunction with a filter capacitor in order to provide a steady and increased DC bias voltage to the emitter, while also coupling a modulated AC carrier signal to the emitter without significant signal attenuation. This self-bias emitter circuit can also include a zener diode to limit the amplitude of the DC bias voltage applied across the emitter.

The disclosed embodiments of a self-bias emitter circuit can use the amplitude of the modulated or unmodulated carrier signal to provide suitable DC bias voltage across the emitter, eliminating the necessity of auxiliary power supplies and external wires, and thereby, reducing operational costs and simplifying operation of the emitter system. Additional features and advantages can become apparent from the detailed descriptions which follow, taken in conjunction with the accompanying drawings.

BRIEF DESCRIPTION OF THE FIGURES

Non-limiting embodiments of the present invention are described by way of example with reference to the accompanying figures which are schematic and are not intended to be drawn to scale. Unless indicated as representing the background information, the figures represent aspects of the invention.

DETAILED DESCRIPTION

In the following detailed description, reference is made to the accompanying drawings, which form a part hereof. In the drawings, which are not to scale or to proportion, similar symbols typically identify similar components, unless context dictates otherwise. The illustrative embodiments described in the detailed description, drawings and claims, are not meant to be limiting. Other embodiments can be used and/or and other changes can be made without departing from the spirit or scope of the present disclosure.

Definition of Terms

As used herein, "emitter" can refer to a device capable of emitting ultrasonic signals and that can be integrated in a self-bias emitter circuit.

As used herein, "self-bias emitter circuit" can refer to a circuit capable of transforming an input modulated or unmodulated AC carrier signal into a steady DC bias voltage.

As used herein, "DC bias voltage" can refer to a steady or constant DC voltage that can be obtained after rectification and filtering of a modulated or unmodulated AC carrier signal, for subsequent application across the emitter.

Description

Figure 1:
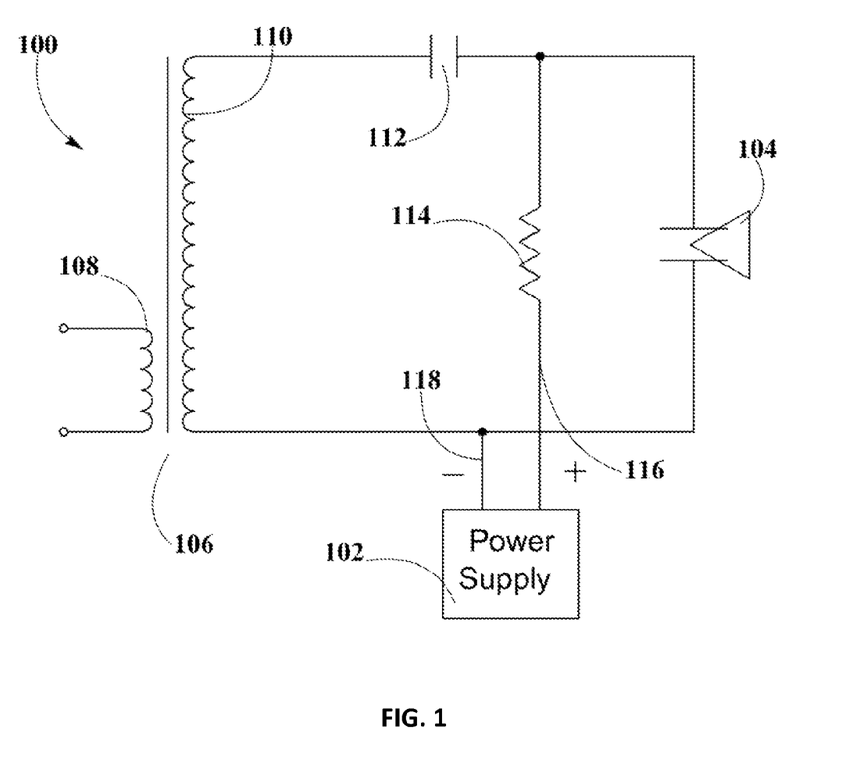
FIG. 1 shows an emitter circuit which can include an auxiliary power supply for supplying a bias voltage across an emitter device as described in the background information.

FIG. 1 shows an emitter circuit 100 which can include an auxiliary power supply 102 for supplying a bias voltage across an emitter 104 as described in the background information. This emitter circuit 100 can also include a transducer 106 with primary 108 and secondary 110, a swing capacitor 112, and a resistor 114.

Emitter 104 can be configured for allowing the emission of ultrasonic signals, and can exhibit a capacitance ranging from about 0.5 nF to about 10 nF depending on materials and configuration of emitter 104. For suitable operation, auxiliary power supply 102 can be operatively coupled to provide a bias voltage across emitter 104 using a first wire 116 and a second wire 118 as shown in FIG. 1. A resistor 114 can be in series with first wire 116 to couple emitter 104. Auxiliary power supply 102 can be powered by a 3V battery to provide an output DC (direct current) voltage that can be constant and can exhibit values ranging from about 200 volts to about 500 volts, depending on the biasing requirements of emitter 104. Optionally, auxiliary power supply 102 can be powered by regular AC (alternating current) 120 volts, in which case an AC/DC transformer can be integrated into auxiliary power supply 102 to convert AC voltage to DC voltage necessary for biasing emitter 114. Resistor 114 can range from about 1 MΩ to about 10 MΩ depending on the coupling requirements of emitter 104.

Capacitor 112 can be installed in emitter circuit 100 to prevent DC bias voltage provided by auxiliary power supply 102 from flowing back to secondary 110, thereby reducing or mitigating interference of auxiliary power supply 102 to the resonance of emitter circuit 100. Preferred value of capacitor 112 can be sufficiently large compared to capacitance exhibited by emitter 104. According to an embodiment, capacitor 112 can range from about 100 nF to about 0.1 µF, as compared to emitter 104 which can typically have a capacitance of about 4 nF to about 8 nF; so the value of capacitor 112 should be substantially greater so as to not lose significant signal there.

Transductor 106 can exhibit a pot core that is inherently shielded to prevent electromagnetic interference or unwanted radiation. Primary 108 can be operatively connected to an amplifier (not shown in FIG. 1) which can feed a carrier signal into emitter circuit 100. Carrier signal can exhibit a sinusoidal AC waveform which periodically reverses direction and can be modulated with an input audio signal processed in a signal processing system (not shown in FIG. 1). Primary 108 can have enough number of turns to match impedance of the amplifier which can typically range between about 4Ω and 12Ω. Secondary 110 can include an inductor which can be selected to match impedance of emitter 104.

As seen from FIG. 1, auxiliary power supply 102 can be needed to supply a DC bias voltage to emitter 104 for suitable operation, along with additional wires 116, 118 which are usually external to emitter circuit 100. These elements can imply additional operational costs to emitter circuit 100.

Figure 2:
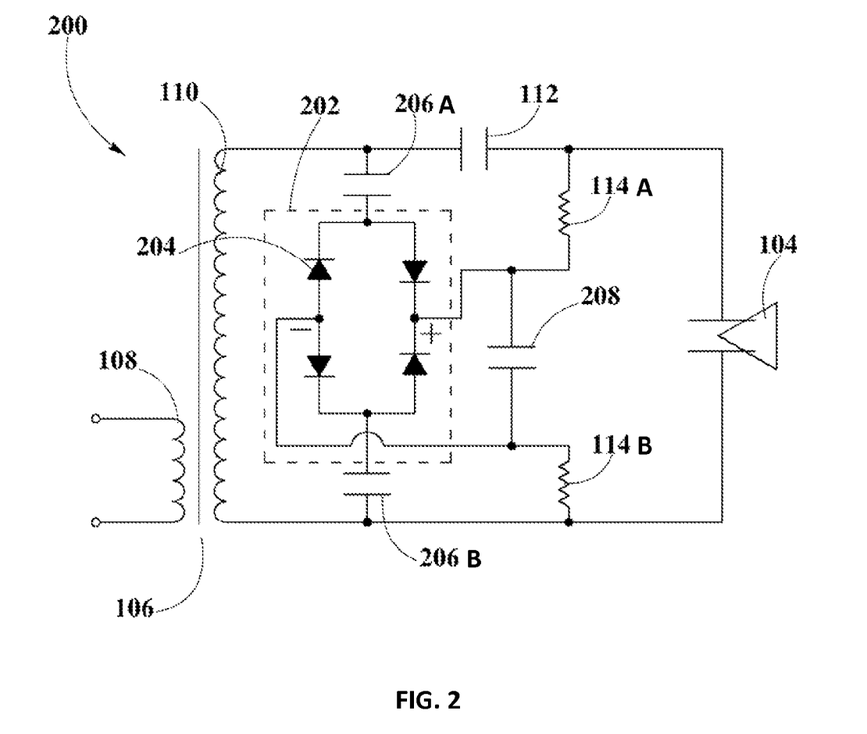
FIG. 2 illustrates a self-bias emitter circuit that can include a full-wave bridge rectifier and does not require the use of auxiliary power supply and wires to provide a DC bias voltage to the emitter, according to an embodiment.

Referring now to FIG. 2, a self-bias emitter circuit 200 does not require the use of auxiliary power supply 102 and wires 116, 118 to provide DC bias voltage to emitter 104, according to an embodiment.

Self-bias emitter circuit 200 can include a full-wave bridge rectifier 202 which can convert the AC carrier signal received by primary 108 to DC voltage. Full-wave bridge rectifier 202 can include 4 diodes 204 which can be configured as shown in FIG. 2 to provide full-wave rectification of AC carrier signal. Two decoupling capacitors 206 A and 206 B can be placed at each side of full-wave bridge rectifier 202 to decouple the DC voltage generated after full-wave rectification. Decoupling capacitors 206 A and 206 B can be small enough to minimize current consumption from full-wave bridge rectifier 202 and to avoid shunting the AC carrier signal, preferably in the range of about 0.001 µF.

While full-wave bridge rectifier 202 can provide unidirectional voltage, this DC voltage cannot have yet reached a constant or steady state. In order to provide a steady DC voltage from the rectified AC carrier signal, a filter capacitor 208 can be operatively coupled to the output of full-wave bridge rectifier 202. Given that the frequency of a carrier signal can be generally high, specifically in the range of about 25 kHz to about 60 kHz, filter capacitor 208 can be sufficiently small, preferably between about 0.01 µF and about 10 µF. This relatively small filter capacitor 208 cannot represent a considerable operational cost to self-bias emitter circuit 200.

Although filter capacitor 208 can provide a sufficiently steady DC voltage, this DC voltage cannot be completely smooth as some ripples can still be present, where these ripples cannot significantly affect suitable operation of emitter 104.

A sufficiently steady DC output voltage can now be across filter capacitor 208 and can be floating because of decoupling capacitors 206 A and 206 B. Two resistors 114 A and 114 B can be operatively coupled with filter capacitor 208 to apply suitable DC bias voltage across emitter 104. Similarly as emitter circuit 100 shown in FIG. 1, self-bias emitter circuit 200 can include capacitor 112 to prevent the DC bias voltage generated by full-wave bridge rectifier 202 from flowing back to secondary 110. In addition, primary 108 can be configured to match impedance of amplifier (not shown in FIG. 2), while secondary 110 can be selected to match impedance of emitter 104.

In another embodiment, it is possible to eliminate either decoupling capacitor 206 B or resistor 114 B from self-bias emitter circuit 200 without compromising performance. In such case, primary 108 can be completely isolated from earth ground or amplifier ground, thus no additional isolation is needed in the form of decoupling capacitor 206 B or resistor 114 B.

Figure 3A:
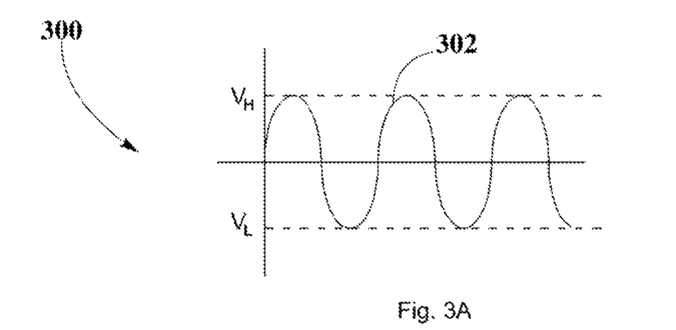
FIGS. 3A, 3B and 3C depict various examples of AC to DC conversion that can be performed by a self-bias emitter circuit.
Figure 3B:
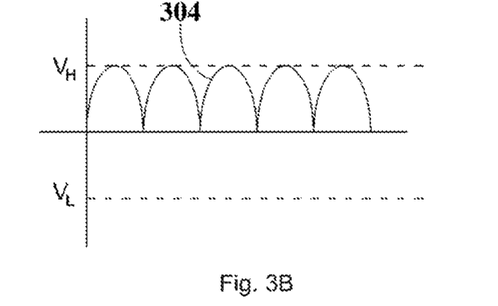
Figure 3C:
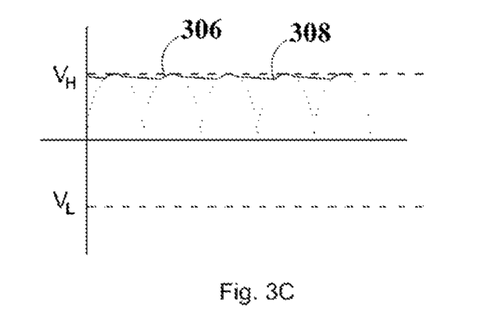

FIG. 3 illustrates an example of AC to DC conversion 300 that can be performed by self-bias emitter circuit 200. This AC to DC conversion 300 can be also applicable to other embodiments of self-bias emitter circuits as described herein.

In FIG. 3A, an exemplary AC carrier signal 302 can be the input at primary 108 and can swing from high voltage $V_H$ to low voltage $V_L$, where $V_H$ can represent the highest peak of the AC carrier signal 302, while $V_L$ can represent its corresponding lowest peak. As such, amplitude of AC carrier signal 302 can be determined by $V_H+V_L$. According to an embodiment, amplitude of AC carrier signal 302 with 0% modulation or no input audio signal can exhibit amplitude of about 150 volts. When this AC carrier signal 302 is near 100% modulated or mixed with another input audio signal, amplitude can increase to a range of about 300 volts to about 600 volts.

FIG. 3B shows full-wave rectified AC carrier signal 304 that can be measured at the output of full-wave bridge rectifier 202. In this full-wave rectified AC carrier signal 304, the $V_L$ swings of AC carrier signal 302 can be rectified to $V_H$, thereby obtaining a signal with unidirectional voltage. However, as shown in FIG. 3B, $V_H$ peaks of full-wave rectified AC carrier signal 304 cannot yet exhibit a steady or constant DC output.

Referring now to FIG. 3C, a steady DC bias voltage 306 can be obtained after filter capacitor 208 decreases the variations of full-wave rectified AC carrier signal 304. Some variations can be still present in steady DC bias voltage 306 in the form of ripples 308. However, these ripples 308 can be minimal and cannot significantly affect suitable application of steady DC bias voltage 306 to emitter 104.

Suitable steady DC bias voltage 306 can be obtained with 0% modulation or unmodulated AC carrier signal 302, where amplitude of steady DC bias voltage 306 can correspond to about $V_H$ peak of AC carrier signal 302 with 0% modulation. According to an embodiment, maximum magnitude of steady DC bias voltage 306 applied to emitter 104 can correspond to maximum $V_H$ peak of 100% modulation or modulated AC carrier signal 302. As such, self-bias emitter circuit 200 described herein can operate with AC carrier signal 302 with 0% modulation or with 100% modulation.

Figure 4:
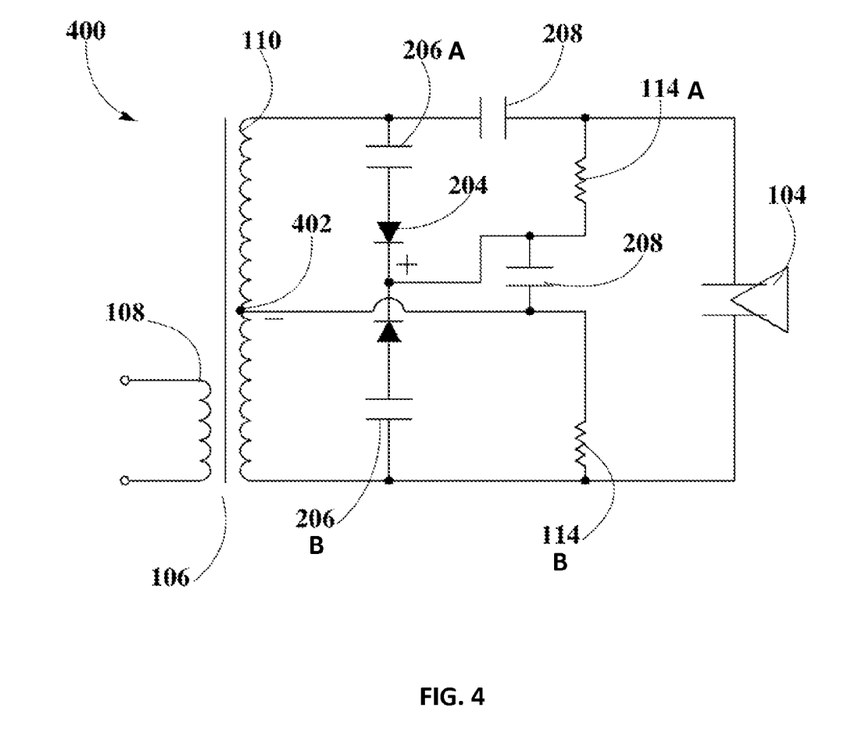
FIG. 4 shows another self-bias emitter circuit that can include a center tapped inductor in conjunction with two diodes for rectification and does not require the use of an auxiliary power supply and wires to provide a DC bias voltage to the emitter.

FIG. 4 shows another self-bias emitter circuit 400 that does not require the use of auxiliary power supply 102 and wires 116, 118 to provide DC bias voltage to emitter 104, according to an embodiment. Self-bias emitter circuit 400 can exhibit same or similar performance as compared to self-bias emitter circuit 200 with the difference that self-bias emitter circuit 400 does not need full-wave bridge rectifier 202 to provide rectification of AC carrier signal.

Self-bias emitter circuit 400 can include transductor 106 with primary 108 matched to amplifier (not shown in FIG. 4) and secondary 110 matched to emitter 104. Secondary 110 can include a center tapped inductor which can deliver half-voltage cycles between center tap 402 and each end of secondary 110, where these half-voltage cycles between center tap 402 and each end of secondary 110 can exhibit opposite polarities. Diodes 204 can provide rectification of both half-voltage cycles across secondary 110, where center tap 402 represent negative output (−), while positive output (+) can be obtained between diodes 204 as shown in FIG. 4. Similarly as in self-bias emitter circuit 200, decoupling capacitors 206 A and 206 B can be placed between secondary 110 and diodes 204 to decouple the DC voltage generated after full-wave rectification.

Output (+/−) can be a DC voltage which can require filtering in order to achieve a constant or steady state. As such, filter capacitor 208 can filter output (+/−) and can be operatively connected to resistors 114 A and 114 B to apply steady DC bias voltage across emitter 104. Capacitor 112 can still be needed to prevent DC bias voltage applied across emitter 104 from flowing back to secondary 110.

Figure 5:
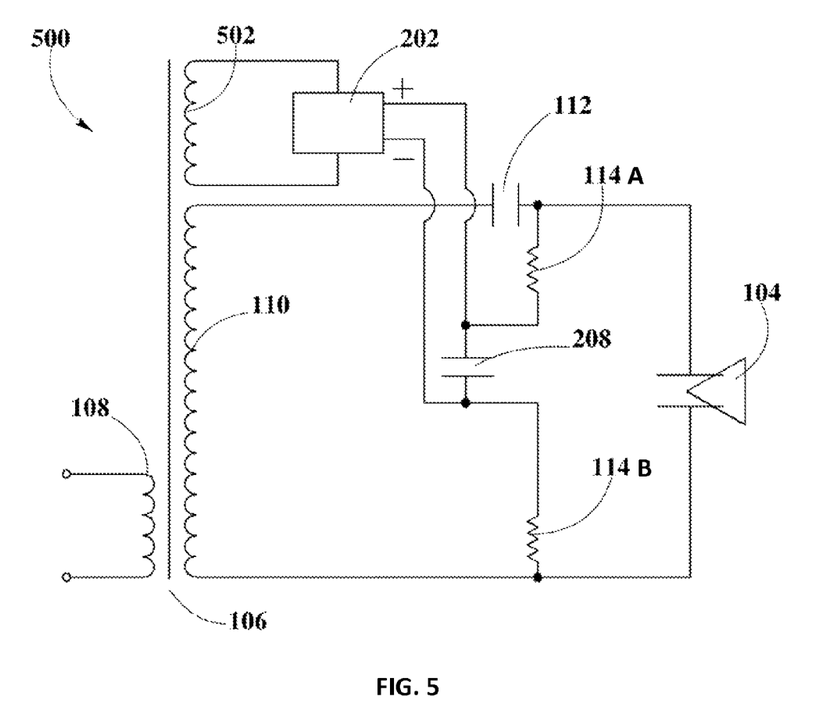
FIG. 5 illustrates another embodiment of a self-bias emitter circuit where a full-wave bridge rectifier can be used in conjunction with an additional secondary to provide a steady DC bias voltage to the emitter.

FIG. 5 shows another embodiment of a self-bias emitter circuit 500 where full-wave bridge rectifier 202 can be used in conjunction with an additional secondary 502 to provide steady DC bias voltage to emitter 104.

Self-bias emitter circuit 500 can include a transductor 106 with primary 108 matched to amplifier (not shown in FIG. 5) and secondary 110 matched to emitter 104. According to some aspects of this embodiment, transductor 106 can also include additional secondary 502 which can share the same magnetically shielded pot core. Number of turns for additional secondary 502 can be selected according to the application. For example, number of turns in additional secondary 502 can be configured for step-up or step-down operation depending on the required levels of DC bias voltage.

Additional secondary 502 can be operatively coupled to full-wave bridge rectifier 202 to convert AC carrier signal received at primary 108 into DC voltage. Subsequently, this DC voltage output from full-wave bridge rectifier 202 can be smoothed by filter capacitor 208 and applied across emitter 104 through resistors 114 A and 114 B. Self-bias emitter circuit 500 cannot include decoupling capacitors 206 A and 206 B (as compared to FIG. 2 and FIG. 4) because voltages at secondary 110 and additional secondary 502 can be isolated from each other. However, capacitor 112 can still be needed to prevent DC bias voltage applied across emitter 104 from flowing back to secondary 110.

Figure 6:
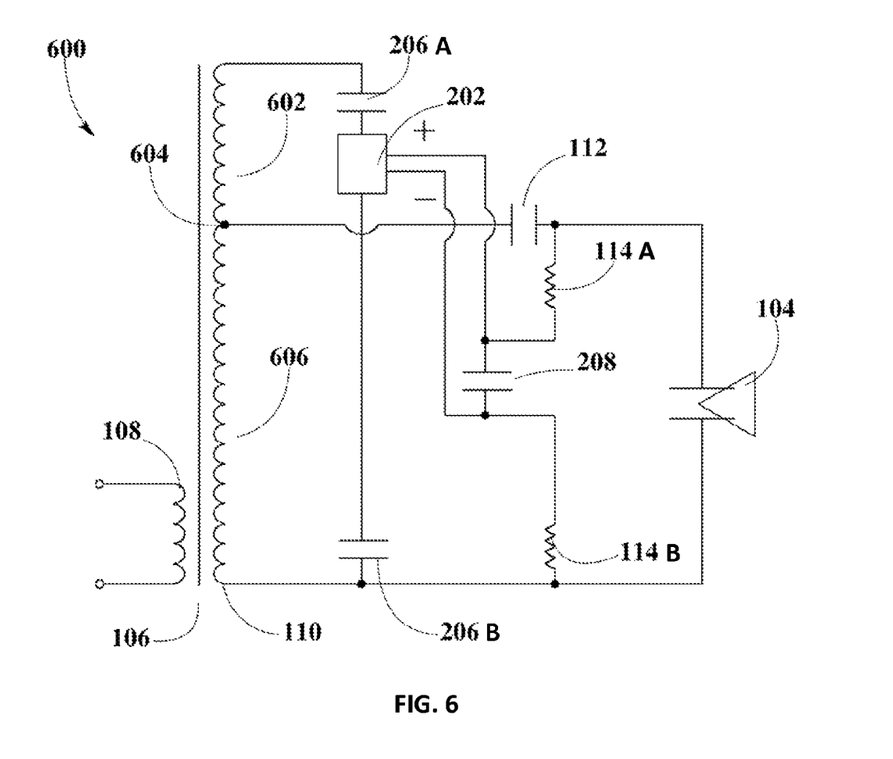
FIG. 6 depicts another embodiment of a self-bias emitter circuit which can include a secondary in the form of an inductor having a section with a higher number of turns and including an intermediate tap, where the section can be connected with full-wave bridge rectifier to provide a steady DC bias voltage to the emitter.

Referring now to FIG. 6, another embodiment of a self-biased emitter circuit 600 can include secondary 110 in the form of an inductor having a section 602 with a higher number of turns and including an intermediate tap 604, where section 602 can be operatively connected with full-wave bridge rectifier 202 to provide steady DC bias voltage to emitter 104.

In self-bias emitter circuit 600, primary 108 can be configured to match amplifier (not shown in FIG. 6), while intermediate tap 604 can configure secondary 110 into two sections, namely section 602 and section 606. Section 602 can exhibit a higher number of turns compared to section 606, in which case, section 602 can provide step-up voltage to full-wave bridge rectifier 202 as required by the application. Optionally, section 602 can be configured to provide step-down voltage to full-wave bridge rectifier 202. Section 606, in the other hand, can be configured with a suitable number of turns to match emitter 104.

Full-wave bridge rectifier 202 can convert AC carrier signal at section 602 into a DC voltage, while filter capacitor 208 can filter this DC voltage and can be operatively connected to resistors 114 A and 114 B to provide a steady DC bias voltage across emitter 104. In this embodiment, decoupling capacitors 206A and 206B can be installed at each side of full-wave bridge rectifier 202 in order to decouple from secondary 110. Similarly to previous embodiments, capacitor 112 can be required to prevent DC bias voltage applied across emitter 104 from flowing back to section 606 of secondary 110.

Figure 7:
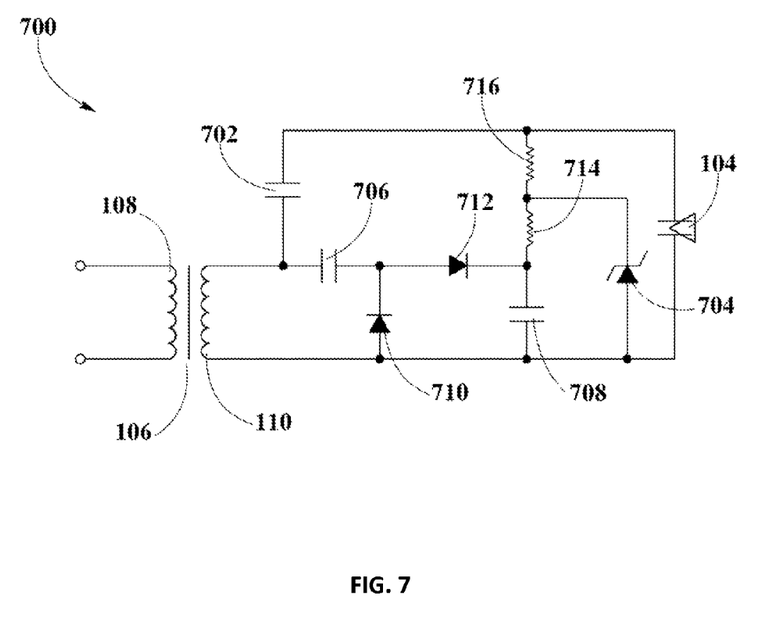
FIG. 7 shows another embodiment of a self-bias emitter circuit which can include a voltage doubler and a zener diode.

FIG. 7 illustrates another embodiment of a self-bias emitter circuit 700 where a voltage doubler can be used in conjunction with a filter capacitor 702 in order to provide a steady and increased DC bias voltage to emitter 104, while also coupling a modulated AC carrier signal to emitter 104 without significant signal attenuation. Self-bias emitter circuit 700 can also include a zener diode 704 to limit the amplitude of the DC bias voltage applied across emitter 104.

In self-bias emitter circuit 700, primary 108 can be matched to amplifier (not shown in FIG. 7), while secondary 110 can be matched to emitter 104. Voltage doubler can include capacitors 706 and 708, along with diodes 710 and 712. A modulated or unmodulated AC carrier signal can be received at secondary 110. During the negative or $V_L$ swing of this AC carrier signal, diode 710 can begin to conduct, causing capacitor 706 to charge; at the same time, diode 712 can be reverse biased, preventing the charging of capacitor 708. Conversely, during the positive or $V_H$ swing of the AC carrier signal, diode 710 can be reverse biased, while diode 712 can begin to conduct, thereby charging capacitor 708. With both capacitors 706 and 708 charged, the DC bias voltage across capacitor 708 can be doubled. According to an embodiment, values for capacitors 706 and 708 can be determined based on the frequency of the AC carrier signal. For example, in case of an AC carrier frequency between about 40 kHz and 50 kHz, capacitors 706 and 708 can typically exhibit a capacitance of about 0.01 μF. In addition, capacitor 706 can prevent the DC bias voltage from flowing back to secondary 110.

Given that the amplitude of the modulated AC carrier signal can change significantly as music content is played, a zener diode 704 can be installed between resistors 714 and 716 to regulate the maximum amplitude of the DC bias voltage applied to emitter 104. For example, a 300 volts zener diode 704 can limit the amplitude of the DC bias voltage across emitter 104 to about 300 volts. The maximum amplitude of the DC bias voltage that can be applied to emitter 104 can be determined based on the materials and thickness of emitter 104 film.

Resistors 714 and 716 can be installed as shown in FIG. 7 to decouple the DC bias voltage and for preventing it from shorting to the AC carrier signal. Resistor 714 decouples zener diode 704 from the voltage doubler, while resistor 716 decouples the regulated DC bias voltage from zener diode 704 to emitter 104. In addition, resistor 716 also decouples the AC carrier signal from having any effect on the DC bias voltage applied across emitter 104. Resistors 714 and 716 can exhibit values ranging from about 330 kΩ to about 1 MΩ.

A filter capacitor 702 can be installed as shown in FIG. 7 for smoothing the DC bias voltage applied across emitter 104. Filter capacitor 702 also provides an effective and continuous electrical path for the AC carrier signal, specifically from secondary 110 to the output or emitter 104, without significant signal attenuation. Filter capacitor 702 can exhibit a capacitance of about 5 μF, depending on the filtering requirements of the DC bias voltage applied across emitter 104. Optionally, a diode (not shown in FIG. 7) can be installed in parallel with filter capacitor 702 in order to prevent any spark from flowing back to filter capacitor 702, and also for preventing filter capacitor 702 from switching to wrong or undesired polarity.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

I claim:

1. An emitter circuit in a parametric loudspeaker for providing a bias voltage, the emitter circuit comprising:
   an emitter configured to emit ultrasonic signals;
   a full-wave bridge rectifier configured to convert an alternating current (AC) carrier signal into a corresponding direct current (DC) voltage; and
   a filter capacitor configured to reduce variations of the DC voltage at an output of the full-wave bridge rectifier in order to provide a DC bias voltage across the emitter, wherein the DC bias voltage is applied across the emitter without affecting carrier information used by the emitter to emit parametric information.

2. The emitter circuit of claim 1, wherein the circuit is configured to receive the AC carrier signal as input and rectify the AC carrier signal into a steady DC bias voltage.

3. The emitter circuit of claim 1, further comprising a transductor with a primary winding and a secondary winding, the transductor configured to match an impedance of the primary winding to an impedance of an amplifier with the secondary winding configured to form a part of a parallel resonant circuit with the emitter.

4. The emitter circuit of claim 3, further comprising a decoupling capacitor configured to decouple the DC bias voltage from the secondary winding and to avoid shunting the AC carrier signal into the full-wave bridge rectifier.

5. The emitter circuit of claim 3, further comprising a capacitor configured to prevent the DC bias voltage from flowing back to the secondary winding.

6. The emitter circuit of claim 2, wherein the AC carrier signal includes a modulated AC carrier signal or an unmodulated AC carrier signal.

7. The emitter circuit of claim 1, wherein the DC bias voltage can correspond with a peak of the AC carrier signal.

8. An emitter circuit in a parametric loudspeaker for providing a bias voltage, comprising:
   an emitter configured to emit ultrasonic signals;
   a transductor including a primary winding and a secondary winding, the secondary winding including a first portion and a second portion;
   a full-wave bridge rectifier coupled to the second portion of the secondary winding, the full-wave bridge rectifier operable to convert an alternating current (AC) carrier signal into a corresponding direct current (DC) voltage; and
   a filter capacitor configured to smooth the corresponding DC voltage in order to provide a DC bias voltage across the emitter.

9. The emitter circuit of claim 8, wherein a number of turns of the first portion of the secondary winding and the second portion of the second secondary winding is determined based on a desired amplitude of the DC bias voltage.

10. The emitter circuit of claim 8, wherein the transductor is configured to:
    match an impedance of the primary winding to an impedance of an amplifier with the secondary winding configured to form a part of a parallel resonant circuit with the emitter.

11. The emitter circuit of claim 10, wherein the step-up voltage conversion provides the DC bias voltage across the emitter.

12. The emitter circuit of claim 8, wherein the emitter circuit includes a center tapped inductor to provide full-wave rectification of the AC carrier signal.

13. The emitter circuit of claim 8, wherein the emitter circuit includes a voltage doubler used in conjunction with the filter capacitor for providing the DC bias voltage to the emitter.

14. The emitter circuit of claim 8, further comprising a diode to limit an amplitude of the DC bias voltage applied across the emitter.

15. A method for providing a bias voltage across an emitter, the method comprising:
 receiving an alternating current (AC) carrier signal at an emitter circuit, the emitter circuit including a transductor with a primary winding and a secondary winding, the emitter circuit being included in a parametric loudspeaker;
 converting the AC carrier signal into a corresponding direct current (DC) voltage; and
 reducing variations of the DC voltage to provide a DC bias voltage across the emitter included in the emitter circuit, the emitter being configured to emit ultrasonic signals.

16. The method of claim 15, further comprising:
 matching an impedance of the primary winding to an impedance of an amplifier; and
 configuring the secondary winding to form a part of a parallel resonant circuit with the emitter.

17. The method of claim 16, further comprising decoupling the DC bias voltage from the secondary winding to avoid shunting the AC carrier signal into a full-wave bridge rectifier associated with the emitter circuit.

18. The method of claim 16, further comprising preventing the DC bias voltage from flowing back to the secondary winding of the transductor.

\* \* \* \* \*